(12) United States Patent
Hathaway et al.

(10) Patent No.: US 11,006,824 B2
(45) Date of Patent: May 18, 2021

(54) ANGULAR SEPARATION OF SCAN CHANNELS

(71) Applicant: Cellview Imaging Inc., Toronto (CA)

(72) Inventors: Mark Hathaway, Canterbury (GB); Rishard Weitz, Toronto (CA)

(73) Assignee: CELLVIEW IMAGING INC.

( * ) Notice: Subject to any disclaimer, the term of this patent is extended or adjusted under 35 U.S.C. 154(b) by 0 days.

(21) Appl. No.: 15/318,221

(22) PCT Filed: Jun. 11, 2015

(86) PCT No.: PCT/CA2015/000371
§ 371 (c)(1),
(2) Date: Dec. 12, 2016

(87) PCT Pub. No.: WO2015/188255
PCT Pub. Date: Dec. 17, 2015

(65) Prior Publication Data
US 2017/0112375 A1   Apr. 27, 2017

Related U.S. Application Data

(60) Provisional application No. 62/010,689, filed on Jun. 11, 2014.

(51) Int. Cl.
*A61B 3/10*   (2006.01)
*G02B 26/10*  (2006.01)
(Continued)

(52) U.S. Cl.
CPC .......... *A61B 3/1025* (2013.01); *A61B 3/0008* (2013.01); *A61B 3/0025* (2013.01);
(Continued)

(58) Field of Classification Search
CPC ......... A61B 3/14; A61B 3/1225; A61B 3/152; A61B 3/10; A61B 3/12; A61B 3/1025;
(Continued)

(56) References Cited

U.S. PATENT DOCUMENTS 8,593,637 B2    11/2013  Folkenberg et al.
9,924,862 B2 *   3/2018  Brown ................. A61B 3/1015
(Continued)

FOREIGN PATENT DOCUMENTS

CA         2881936 A1    4/2014
CN       103908223 A     7/2014
(Continued)

OTHER PUBLICATIONS

A.G. Podoleanu, Combining SLO and OCT Technology, Bull. Soc. beige Ophtalmol, 302, 133-151, 2006.

*Primary Examiner* — Jie Lei
(74) *Attorney, Agent, or Firm* — Laubscher & Laubscher, P.C.

(57) ABSTRACT

Channel separation in ophthalmologic systems is achieved by introducing a small angle between each beam incident on the scanner. The multiple channels are emitted from multiple emitters positioned such that their respective beams reach an X-Y scanner with small angular separations between the beams. This removes the need for dichroic components to combine the multiple channels into a single beam. This also allows the emitters to use the same wavelength if desired, such as in a combined SLO and OCT system in which it may be desirable to use the same light source in order to reduce the cost and complexity of the system.

11 Claims, 2 Drawing Sheets

(51) Int. Cl.
  *A61B 3/00* (2006.01)
  *A61B 3/12* (2006.01)
  *G02B 26/12* (2006.01)
  *G01B 9/02* (2006.01)

(52) U.S. Cl.
  CPC ............... *A61B 3/102* (2013.01); *A61B 3/12* (2013.01); *G01B 9/02019* (2013.01); *G01B 9/02027* (2013.01); *G01B 9/02091* (2013.01); *G02B 26/101* (2013.01); *G02B 26/123* (2013.01); *G01B 2290/45* (2013.01); *G01B 2290/65* (2013.01)

(58) Field of Classification Search
  CPC ......... A61B 3/113; A61B 3/1015; A61B 3/00; A61B 3/102; A61B 3/0025; A61B 3/103; A61B 3/107; A61B 5/1455; A61B 5/14532; A61B 6/032; A61B 5/16; A61B 3/0008; G02B 26/10; G02B 26/101; G02B 26/123; G01B 9/02027; G01B 9/02091; G01B 9/02019; G01B 2290/45; G01B 2290/65

USPC ....... 351/206, 205, 208, 210, 212, 221, 246; 600/318, 319, 425, 558
  See application file for complete search history.

(56) References Cited

U.S. PATENT DOCUMENTS

2007/0189664 A1* 8/2007 Andersen ................ A61F 9/008
  385/25
2011/0273668 A1* 11/2011 Hirose .................... A61B 3/102
  351/206

FOREIGN PATENT DOCUMENTS

WO   2007082102 A2   7/2007
WO   2011093061 A1   8/2011

* cited by examiner

ANGULAR SEPARATION OF SCAN CHANNELS

FIELD OF INVENTION

This invention relates to ophthalmology, and in particular to the use of multiple scan channels.

BACKGROUND

This idea relates to an issue that arises frequently in both scanning laser ophthalmoscopy (SLO) systems and optical coherence tomography (OCT) systems. There is usually a need to combine multiple scan channels before they enter a patient's eye. Examples of multiple channels could be different wavelength SLO channels, or an SLO channel combined with an OCT channel.

The various scan channels are typically combined before entering the patient's eye. The light returning from the patient's eye is then separated again into the channels such that it can be processed in a manner appropriate to that channel. To reduce system costs a single X-Y scanner is used for all the channels.

A commonly used technique when the channels use different wavelengths is illustrated in FIG. 1. The different wavelengths are combined with dichroic beam splitters, then the collimated beam is launched at a scanning mechanism. This collimated beam is reflected from the patient's eye and re-enter the scanner and directed back towards to dichroic splitters. The dichroic splitters are then re-used to separate the returned light from the patient, and direct beams of particular frequencies back to the respective emitters. The beams shown in FIG. 1 (each using a different pattern of dashes, for clarity) are shown separated for clarity, but in reality they would be collinear. However there are a number of issues with the chromatic combination and separation of each channel.

First, each channel must use a separate wavelength. This is not such an issue for a purely SLO system employing multiple wavelengths. But in the case of a combined OCT/SLO system it may be desirable to use a single source for both the SLO and OCT systems to reduce both system cost and complexity.

Second, OCT systems require careful control of both the dispersion and the differential group delay. This inevitably results in more complex optical coatings and an increase in component cost.

Third, there is the additional cost of the dichroic components, and the additional manufacturing steps needed to mount and align them.

SUMMARY

The issues with chromatic separation are solved by introducing a small angle between each beam incident on the scanner. The multiple channels are emitted from multiple emitters, but there are no dichroic mirrors to combine the multiple channels into a single beam. Rather the different beams reach the X-Y scanner with small angular separations between the beams.

BRIEF DESCRIPTION OF THE DRAWINGS

The features and advantages of embodiments of the invention will become more apparent from the following detailed description of the preferred embodiment(s) with reference to the attached figures, wherein.

It is noted that in the attached figures, like features bear similar labels.

DETAILED DESCRIPTION OF THE PREFERRED EMBODIMENTS

Figure 1:
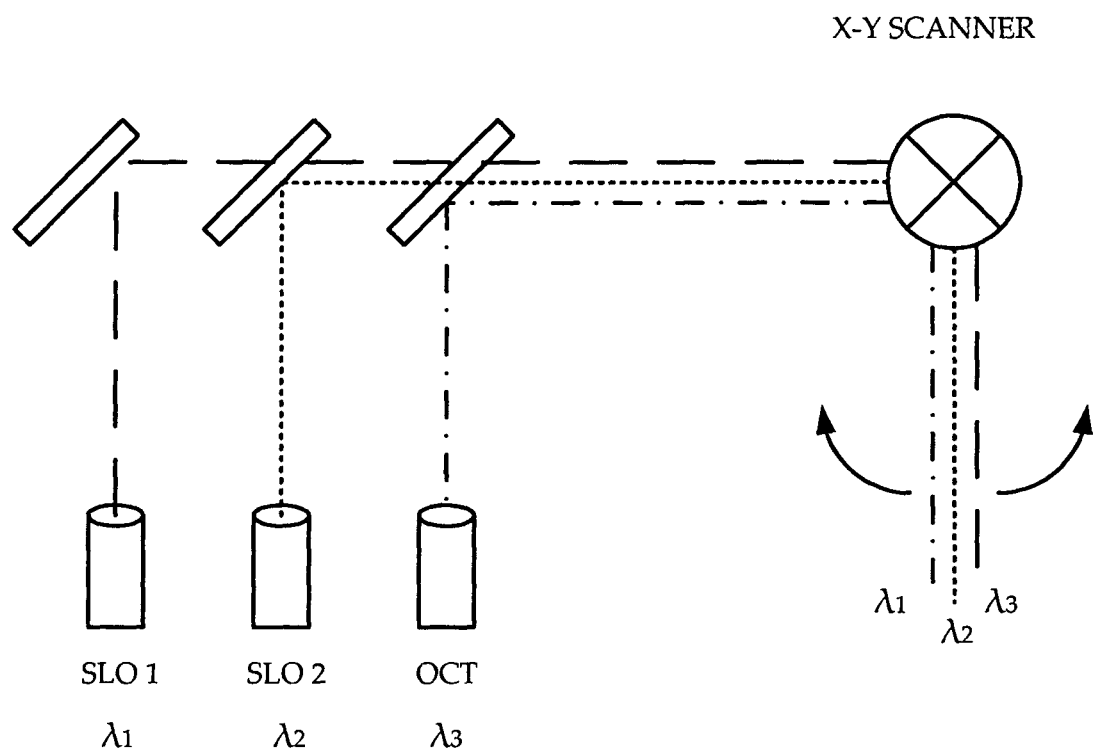
FIG. 1 shows an arrangement of multiple emitters.
Figure 2:
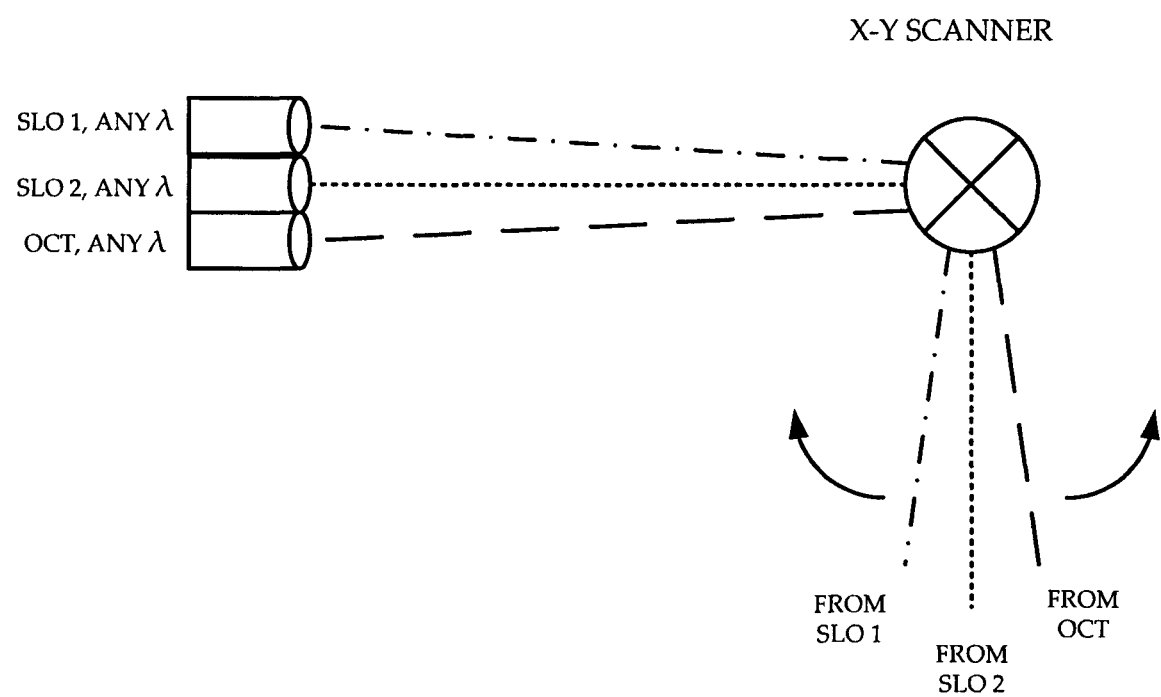
FIG. 2 shows an arrangement of multiple emitters according to one embodiment of the invention.

Referring to FIG. 2, an arrangement of multiple emitters according to one embodiment of the invention is shown. Emitters for two SLO wavelengths and for one OCT wavelength, which may of course be the same as one of the two SLO wavelengths, are shown. More generally there are at least two emitters, any number of which or none of which is used in an SLO system, and any number of which or none of which is used in an OCT system. In one embodiment, all of the emitters are for an SLO system. The emitters are positioned such that their respective beams reach an X-Y scanner at a slight angular separation. The beams from each emitter are shown using different patterns of dashes for clarity only.

The X-Y scanner reflects the beams towards a patient's eye. As the beams are not collimated with each other as they enter the X-Y scanner, there remains an angular separation of the beams from the X-Y scanner to the patient's eye.

The beams reflected from the eye will reverse their path to a respective detector alongside the respective emitter. The angular separation of the beams upon reaching the eye will of course lead to a displacement in the scanned images of the eye, but because the angular separation of the beams is fixed the images can be realigned so they can be overlaid. In one embodiment, the system of the invention includes a processing module configured to compensate for any displacement of the scanned images. Alternatively, the rotation offset for the scanner required for each channel to image the same point in the retina can be calculated in advance. With this method and system, there is no restriction on the wavelengths used for the channels. If one of the emitted channels is used for OCT purposes, there are no additional dispersion issues for an OCT channel.

Since there are no dichroic mirrors and since the beams from each emitter are not collimated with the beams from the other emitters, beams may have similar wavelengths, and one or more of the emitters may emit tunable wavelengths.

In operation, according to one embodiment, a beam of light is emitted from each of at least two emitters, each of emitters being positioned such that each beam is transmitted at a different angle from each other beam. Each beam thereby reaches the X-Y scanner at a different angle from each other beam. The X-Y scanner reflects the beams towards a patient's eye in order to scan the eye with the beams. The eye reflects beams back towards the X-Y scanner, each reflected beam reaching the X-Y scanner at a different angle. The X-Y scanner reflects the reflected light beams towards at least two receivers, one receiver associated with each emitter, each light beam reflected by the X-Y scanner towards a receiver being reflected at a different angle from each other light beam being reflected by the X-Y scanner towards a receiver.

For each reflected beam received by a receiver, an image is formed. The images are processed in order to compensate for displacement of the images due to the different angles at which the emitted beams reach the patient's eye.

The embodiments presented are exemplary only and persons skilled in the art would appreciate that variations to the embodiments described above may be made without departing from the spirit of the invention. The scope of the invention is solely defined by the appended claims.

We claim:

1. A system for observing a patient's retina using multiple light beams, comprising:
   an X-Y scanner;
   at least two emitters, each emitter transmitting a beam of light directly to the X-Y scanner without using dichroic mirrors or beam splitters, each of the emitters being positioned such that each beam is transmitted at a different angle from each other beam, each beam thereby reaching the X-Y scanner at a different angle from each other beam, each beam reflected by the X-Y scanner at a different angle from each other beam toward a patient's eye; and
   at least one receiver to receive beams reflected from the patient's eye;
   wherein the X-Y scanner scans the beams from the at least two emitters simultaneously to provide multiple separated scan beam paths.

2. The system of claim 1, wherein the X-Y scanner scans the patient's eye.

3. The system of claim 2, further comprising at least two receivers, one receiver associated with each emitter, positioned such that when the X-Y scanner reflects light beams reflected by the patient's eye towards the receivers, the light beam received by each receiver leaves the X-Y scanner at a different angle from each other beam received by one of the receivers.

4. The system of claim 3, further comprising a processing module configured to compensate for displacement of scanned images formed from the light received by the receivers due to the different angles at which the beams reach the patient's eye.

5. The system of claim 1, where at least two of the at least two emitters transmit light beams having substantially the same wavelength.

6. The system of claim 1, wherein the at least two emitters comprise emitters for scanning laser ophthalmologic (SLO), emitters for optical coherence tomography (OCT), or emitters for both SLO and OCT.

7. A method of scanning a patient's retina using multiple light beams, the method comprising:
   emitting a beam of light from each of at least two emitters, each emitter being positioned such that each beam is transmitted at a different angle from each other beam, each beam thereby directly reaching an X-Y scanner at a different angle from each other beam without using dichroic mirrors or beam splitters; and
   reflecting each beam by the X-Y scanner at a different angle from each other beam towards a patient's eye without overlap of the beams;
   wherein the X-Y scanner scans the beams from the at least two emitters simultaneously to provide multiple separated scan beam paths.

8. The method of claim 7, further comprising scanning h patient's eye.

9. The method of claim 8, further comprising:
   receiving at the X-Y scanner light beams reflected by the patient's eye; and
   at the X-Y scanner, reflecting the light beams reflected by the patient's eye towards at least two receivers, one receiver associated with each emitter, each light beam reflected by the X-Y scanner towards a receiver being reflected at a different angle from each other light beam being reflected by the X-Y scanner towards a receiver.

10. The method of claim 9, farther comprising:
    forming at least two images, each image being formed from information in the light beam received by one of the receivers; and
    processing the images in order to compensate for displacement of the images due to the different angles at which beams reach the patient's eye.

11. The method of claim 7, wherein the at least two emitters comprise emitters for scanning laser ophthalmologic (SLO), emitters for optical coherence tomography (OCT), or emitters for both SLO and OCT.

* * * * *